(12) United States Patent
Kamer et al.

(10) Patent No.: US 10,512,546 B2
(45) Date of Patent: Dec. 24, 2019

(54) METHOD FOR MANUFACTURING AN AUXILIARY DEVICE SUITABLE FOR THE MANUFACTURE OF A PATIENT CUSTOMIZED IMPLANT

(71) Applicant: AO Technology AG, Chur (CH)

(72) Inventors: Lukas Kamer, Schindellegi (CH); David Eglin, Davos Frauenkirch (CH)

(73) Assignee: AO Technology AG, Chur (CH)

( * ) Notice: Subject to any disclaimer, the term of this patent is extended or adjusted under 35 U.S.C. 154(b) by 0 days.

(21) Appl. No.: 15/542,476

(22) PCT Filed: Jan. 12, 2015

(86) PCT No.: PCT/CH2015/000001
§ 371 (c)(1),
(2) Date: Jul. 10, 2017

(87) PCT Pub. No.: WO2016/112469
PCT Pub. Date: Jul. 21, 2016

(65) Prior Publication Data
US 2018/0271661 A1    Sep. 27, 2018

(51) Int. Cl.
*A61F 2/30*    (2006.01)
*A61B 34/10*    (2016.01)
(Continued)

(52) U.S. Cl.
CPC ...... *A61F 2/30942* (2013.01); *A61B 17/8061* (2013.01); *A61B 34/10* (2016.02);
(Continued)

(58) Field of Classification Search
CPC ........ A61F 2/30942; A61F 2002/30939; A61F 2/3094; A61F 2002/30948;
(Continued)

(56) References Cited

U.S. PATENT DOCUMENTS 9,901,463 B2 *  2/2018  Mahfouz .............. A61F 2/461
2003/0216669 A1 * 11/2003  Lang ................... A61B 5/4528
600/587
(Continued)

FOREIGN PATENT DOCUMENTS

KR    20120088928 A    8/2012
RU     2164392 C1    3/2001
(Continued)

OTHER PUBLICATIONS

Jacuiéry, C. et al. "Reconstruction of Orbital Wall Defects: Critical Review of 72 Patients", International Journal of Oral and Maxillofacial Surgery, Mar. 2007, pp. 193-199, vol. 36-Issue 3, Elsevier Inc.

*Primary Examiner* — Alvin J Stewart
(74) *Attorney, Agent, or Firm* — Rankin, Hill & Clark LLP

(57) ABSTRACT

Method for manufacturing an auxiliary device suitable for the manufacture of a patient customized implant comprising the steps of: 1) obtaining 3D image data, preferably a CT of a defect site of a patient's anatomy (1); 2) generating a computer model of the defect site based on the 3D image data and 3D generic reference data by using image processing techniques; 3) virtually reconstructing the defect site; 4) generating a computer template (30) which represents an auxiliary device (40) that is suitable for sizing, shaping and positioning of alloplastic implants; and 5) manufacturing an auxiliary device (40) using 3D printing. Furthermore, there is provided a method for manufacturing a patient customized implant using the auxiliary device and a method for the reconstruction of a particular anatomy by using the manufactured patient customized implant.

22 Claims, 2 Drawing Sheets

(51) Int. Cl.
*A61F 2/28* (2006.01)
*A61B 17/80* (2006.01)

(52) U.S. Cl.
CPC ...... *A61F 2/2875* (2013.01); *A61B 2034/102* (2016.02); *A61B 2034/105* (2016.02); *A61B 2034/108* (2016.02); *A61F 2002/2878* (2013.01); *A61F 2002/30578* (2013.01); *A61F 2002/30948* (2013.01); *A61F 2002/30957* (2013.01); *A61F 2002/30962* (2013.01); *A61F 2310/00023* (2013.01)

(58) Field of Classification Search
CPC .... A61F 2002/3095; A61F 2002/30962; A61F 2002/30968; A61F 2002/3097; A61B 34/10; A61B 2034/102; A61B 2034/104; A61B 2034/108; A61B 17/8061
See application file for complete search history.

(56) References Cited

U.S. PATENT DOCUMENTS

| | | | |
|---|---|---|---|
| 2018/0271602 A1* | 9/2018 | Frey | A61B 34/10 |
| 2018/0271661 A1* | 9/2018 | Kamer | A61B 34/10 |
| 2018/0325526 A1* | 11/2018 | Haddad | G16H 50/50 |

FOREIGN PATENT DOCUMENTS

| | | |
|---|---|---|
| WO | 2012123029 A1 | 9/2012 |
| WO | 2014178706 A1 | 11/2014 |

* cited by examiner

METHOD FOR MANUFACTURING AN AUXILIARY DEVICE SUITABLE FOR THE MANUFACTURE OF A PATIENT CUSTOMIZED IMPLANT

The invention generally relates to a method for the reconstruction of a particular anatomy. More particularly, the present invention relates to a method for manufacturing an auxiliary device suitable for the manufacture of a patient customized implant according to the preamble of claim 1, to an auxiliary device obtained by that method, to a method for manufacturing a patient customized implant using the auxiliary device obtained by that method and a further method for the reconstruction of a particular anatomy by using that patient customized implant.

In the following an example will be given to reconstruct the particular anatomy of an orbital defect creating an auxiliary device to manufacture an orbital implant. However it is understood that the method is not exclusively applicable to the orbital region but also to other skeletal sites.

Orbital defects typically involve the orbital floor and medial wall and induce displacement and dysfunction of orbital soft tissue. These conditions frequently result in significant enophthalmos, impaired eye motility and disturbed binocular vision. A mainstay of surgical treatment is the reconstruction of the preinjury anatomy to reestablish orbital form and function. However this is difficult to achieve especially in large sized defects located in the posterior orbit. Adequate reconstruction must be obtained at primary surgery, as secondary surgery is even more challenging. Limited access and visibility make adequate implant shaping and positioning difficult to achieve.

Traditional surgical techniques for reconstructing orbital wall defects involve freehand contouring and positioning of alloplastic implant or bone grafts which are technically difficult and disposed to error. In the recent past pre-shaped orbital implants and intraoperative imaging and navigation techniques have been used to facilitate the surgical procedure.

From RU 2 164 392 SHALUMOV a method is known for producing individual high precision implants for a treatment of subtotal polyosseous orbital cavity defects. Data received from a computed tomography (CT) information treatment are used for producing orbit volume parameters of the retained tissue and of the tissues with an anatomical defect. After carrying out symmetric mirror computer transformations the parameters are superimposed and difference estimations are used for determining mathematical spatial parameters of an implant the contact surfaces of which are adjusted to fit particular anatomical objects of a patient's cranium, e.g. the frontal process of the process of the maxilla, the zygomatic process of the temporal bone and the process of the frontal bone. The so achieved complete set of mathematical spatial parameters of an individually adjusted implant is exported to an automated prototyping device so as to manufacture the implant.

However, the standard three-dimensional (3D CT) representation of the healthy side as well as of the affected side (fracture/defect) can be severely affected. In particular, this concerns the orbit where frequently fractures occur in the range of the osseous orbital floor and the medial orbital wall. Therefore, in the treatment of orbital fractures the clinical problem is encountered that preshaped orbital implants need to be intraoperatively sized and shaped so that the precise position of the orbital implant can only be defined intraoperatively.

It is therefore an object of the invention to provide an improved method for manufacturing an auxiliary device suitable for the manufacture of a patient customized implant.

The invention solves the posed problem with a method for manufacturing an auxiliary device suitable for the manufacture of a patient customized implant comprising the features of claim 1, with an auxiliary device comprising the features of claim 9, with a method for manufacturing a patient customized implant comprising the features of claims 16 and with a method for the reconstruction of a particular anatomy comprising the features of claim 17.

The advantages of the method according to the invention are to be seen that:
- the manufacture of a patient customized implant is permitted which can consist of one of a variety of biocompatible materials and permits an incorporation of a prefabricated solid matrix portion having screw holes;
- improved 3D CT reconstruction and image mirroring techniques can be used where anatomical information was lost;
- the possibility is offered to anatomically reconstruct the healthy side indirectly as well as the affected side directly by means of 3D anatomical reference data (i.e. by means of a 3D reference model, 3D mean model or 3D atlas model) to manufacture an auxiliary device for the affected site so as to facilitate the adaption of the implant (size, shape and position). Differences in size and shape between the healthy and the affected side can be technically compensated; and
- one or more spacers of a desired shape and volume can be applied to a site where it is necessary to reduce the volume, e.g. the volume of the orbit.

The method according to the invention can be applied in the following medical fields:
1. field of maxillofacial/craniofacial surgery:
   reconstruction of orbital defects (orbital floor, orbital floor/medial wall defects)
   reconstruction of calvarial defects (i.e. for cranioplasty), craniofacial and maxillofacial defects
2. field of orthopedic trauma:
   restoration of bony defects, particularly cortical bone defects
   in combination with minimal invasive surgery approaches
3. field of dental surgery: reconstruction of dentoalveolar defects
4. spine surgery: reconstruction of defects of the spine.

The invention particularly offers a new computerized method for manufacturing an auxiliary device (rapid prototyping device) serving as a reconstruction template allowing for facilitated implant adaption and positioning and for different implant material to be used (i.e. standard titanium implants or biodegradable and biocompatible resin). The method offers the possibility of molding a light curing or self-setting biodegradable and biocompatible resin in a template to form an implant. The method is preferably designed as an in-house workflow requiring no costly and time-consuming external manufacturing.

In order to solve the clinical problem the present invention comprises a sequence of specific workflow steps, necessitating digitized technologies (i.e. techniques for 3D imaging, image processing and analysis) and a rapid prototyping device with specific design features incorporated that allows for shaping as well as positioning of alloplastic implants. Further on the invention comprises a workflow that allows for immediate production of customized alloplastic implants like titanium or even of light curing or self-setting biodegradable and biocompatible resin.

Advantages are seen, e.g. in the primary reconstruction of orbital defects. The computerized method leads to the production of an auxiliary device (reconstruction and positioning template) providing information on an individual implant geometry and on its proper positioning within the orbit. The method according to the invention allows for more efficient implant adaption and does not require repeated checks at the patient site while shaping the implant. It allows for immediate generation of patient specific alloplastic implants immediately available for surgery. There is the choice to produce customized alloplastic implants made out of titanium or of light curing or self-setting biodegradable and biocompatible resin. The use of light curing or self-setting biodegradable and biocompatible resin into the workflow permits for immediate production of organic/degradable implants.

Further advantageous embodiments of the invention can be commented as follows: In a special embodiment the computer template comprises a recess positioned on a surface that is directed towards a defect site, wherein the size of the computer template is larger than the size of the recess.

In a further embodiment the size of the recess is larger than the size of the defect site so as to encompass the shape of a defect.

Preferably, the 3D generic reference data comprise a 3D anatomic atlas and/or the 3D generic reference data is obtained by mirror imaging of the healthy contralateral side and/or the 3D generic reference data comprise a 3D mean shape model, preferably with standard deviation information.

In another embodiment the auxiliary device corresponds to a physical model of the computer template.

In another embodiment the 3D printing technology is a rapid prototyping technology.

In again another embodiment the auxiliary device is designed to be fitted to an unaffected region.

In a further embodiment the auxiliary device is designed to be fitted to the boundaries of the defect and to the respective anatomical shape in this inferior orbital rim region.

In a further embodiment the auxiliary device is designed with a holding extension facilitating manual implantation of the implant.

In another embodiment the auxiliary device has a peripheral projection to be fitted to an unaffected region.

In another embodiment of the auxiliary device the holding extension is designed to allow a standard surgical instrument to be used to manually position the implant.

In yet another embodiment the auxiliary device has a recess suitable to shape and size an implant. This configuration permits the advantage that the auxiliary device can be used as a reconstruction template. This reconstruction template can be used as a mold for the manufacture of an implant (curable biocompatible resin) or as a form allowing for facilitated implant adaption (standard titanium mesh). The auxiliary device therefore permits the manufacture of a patient customized implant which can consist of one of a variety of biocompatible materials and permits an incorporation of a prefabricated solid matrix portion having screw holes.

According to a further aspect of the invention, there is provided a method for manufacturing a patient customized implant using the auxiliary device and comprising the step of: a) introducing a curable biocompatible resin in the recess of the auxiliary device in a moldable state and photocuring the resin once fitted into the recess of the auxiliary device; OR b) press-fitting a standard implant material like a meshed titanium implant into the recess of the auxiliary device.

In accordance with another aspect, a method for the reconstruction of a particular anatomy by using a patient customized implant is provided, the method comprising the additional step of: positioning the implant onto the defect without the auxiliary device; or positioning the implant with a least a part of the auxiliary device.

In a special embodiment of the method the implant is positioned in the recess of the auxiliary device during implantation.

In a further embodiment the method is characterized by the further step of fixing the implant with screws to a patient's anatomy.

In another embodiment the auxiliary device has a peripheral projection to be fitted to an unaffected region and the part of the auxiliary device used for positioning the implant includes the peripheral projection.

In another embodiment the auxiliary device includes a holding extension and the part of the auxiliary device used for positioning the implant includes the holding extension.

In again another embodiment the method comprises the additional step of: removing the auxiliary device.

A BRIEF DESCRIPTION OF THE DRAWINGS

A special embodiment of the invention will be described in the following by way of example and with reference to the accompanying drawings in which:

FIGS. 1-4 illustrate an embodiment of the method for manufacturing an auxiliary device 40 to be used for the subsequent manufacture of a patient customized implant 50 (FIG. 5), wherein the method comprises the steps of:

1) Obtaining a pre-operative standard CT of the affected site and of the healthy contralateral side.

2) Based on preoperative CT and image processing techniques a computer model of the defect site and the respective healthy contralateral site is created. A main technical problem is that the 3D reconstruction process creates pseudo holes mainly due to partial volume averaging with missing anatomical information at the healthy contralateral side as well as at the affected side, i.e. in the orbit mainly located in the orbital floor and the medial wall.

3) The defect site 2 is virtually reconstructed, preferably in an automated way with the preinjury anatomy integrated in an orbital computer model. This step requires anatomical information (i.e. a 3D reference model, a 3D mean model or a 3D atlas model to be used). The virtual reconstruction of the defect site can be performed by the following substeps:

A1) automated reconstruction of the healthy contralateral side using 3D anatomical reference data;
A2) mirror imaging of the reconstructed healthy contralateral side; and
A3) automated reconstruction of the affected side by superposing the mirror imaged reconstructed healthy contralateral side and the affected side one above another resulting in the 3D computer model with the virtually reconstructed defect side;

or alternatively by the following substeps:
B1) automated reconstruction of the healthy contralateral side according to defined landmarks on both sides and extrapolate deviation;
B2) mirror imaging of the reconstructed healthy contralateral side; and
B3) restoration of the affected side by superposing the mirror imaged reconstructed healthy contralateral side and the affected side one above another resulting in the 3D computer model with the virtually reconstructed defect side;

or alternatively by the following substeps:
C1) automated reconstruction of the affected side according to defined landmarks and extrapolate deviation; or
C2) automated reconstruction of the affected side using 3D anatomical reference data; and
C3) restoration of the affected side resulting in the 3D computer model with the virtually reconstructed defect side.

Figure 1:
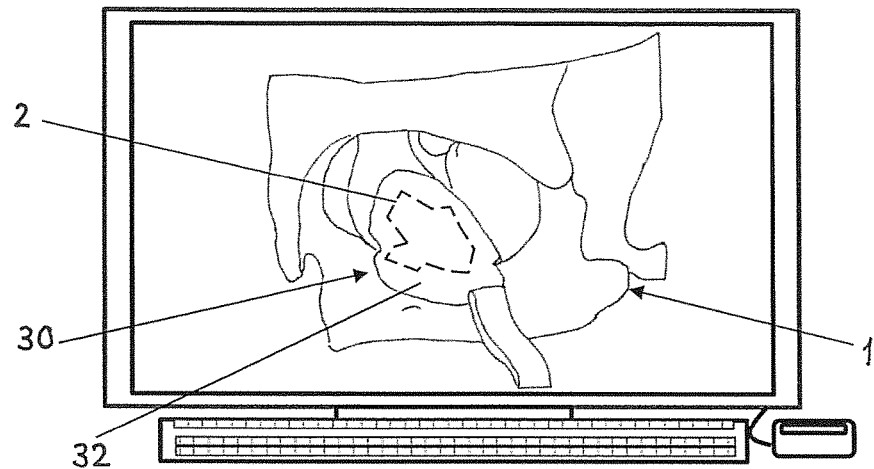
FIG. 1 illustrates a 3D computer model (based on a CT) of an orbital floor defect together with a computer template of the auxiliary device covering the orbital floor defect according to an embodiment of the invention.
Figure 2:
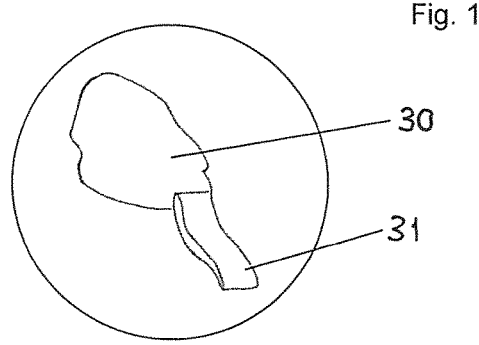
FIG. 2 illustrates a magnified view of the computer template of FIG. 1.

4) Planning and designing of the 3D implant model using the computer.
5) Approval of the designed 3D implant model by the surgeon:
   If the design is approved the procedure proceeds with step 6)
   If the design is not approved step 3 is repeated with alternative options B1-B3 or C1-C3 or with combinations of the options A1-A3, B1-B3 and C1-C3.
6) A computer template 30 (FIG. 1-3) is generated with preferably the following design features incorporated:
   The computer template 30 is:
   (i) covering the defect 2 with an overlay 32,
   (ii) designed with a recess 35, wherein:
      the recess 35 is positioned in the surface which is directed to the orbital defect (FIG. 3), and
      the recess 35 is larger than the defect and encompasses the shape of the defect, so that the size of the computer template 30 is larger than the size of the recess 35 which in turn is larger than the defect size.
   (iii) fitted to an unaffected region (i.e. to the boundaries of the defect and to the inferior orbital rim region), and
   (iv) designed with a holding extension 31.
7) The auxiliary device 40 (physical model) of the computer template 30 is manufactured using 3D printing technologies (i.e. rapid prototyping technologies). The so produced auxiliary device 40 has a shape and size that is larger than the defect size and includes a recess 42 as defined by the recess 35 of the computer template 30, so that the recess 42 of the auxiliary device 40 permits to adapt the size and shape of a titanium mesh which covers the defect.

Furthermore, the auxiliary device 40 can be provided with a peripheral projection the shape and size of which is defined by the overlay 32 of the computer template 30 and which is suitable to be fitted to an unaffected region in the area of the affected region, i.e. with a peripheral projection that is slightly bigger than the defect to be able to design a recess and to achieve reliable positioning within the orbit. Additionally or alternatively, the auxiliary device 40 can include a holding extension 41 which corresponds to the holding extension 31 of the computer template 30 and which is suitable for positioning an implant 50. Since the recess 42 is larger than the defect and since it can be provided with a peripheral projection (i.e. designed as margin), it allows the implant to be sized, shaped and directly positioned onto the defect or allows the adapted implant together with its auxiliary device to be positioned onto the defect. Hence a recess allows an implant to be sized and shaped. A larger recess and a peripheral projection are specific design features to shape, size and position an implant, or to shape, size and position an implant together with the corresponding auxiliary device.

The auxiliary device 40 is preferably manufactured in plastic. The production location is preferably the hospital site as this requires no external third party service to be used. The auxiliary device 40 (resulting rapid prototyping device) may be used to adjust the implant 50 prior to or during surgery.

Figures 3, 4:
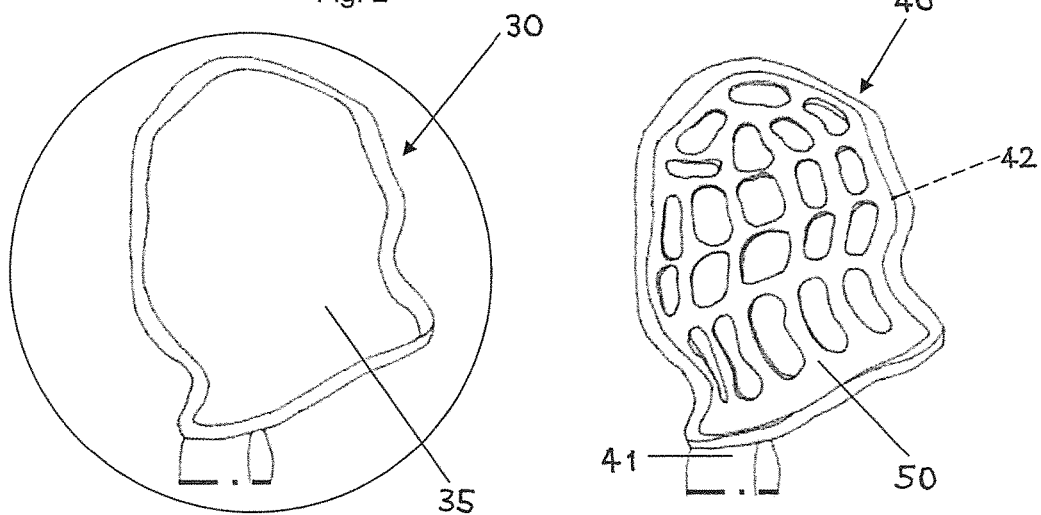
FIG. 3 illustrates the computer template of FIG. 1 in a view onto the surface of the template which is directed to the orbital defect and which includes a recess.
FIG. 4 illustrates an auxiliary device (physical model) based on the computer template of FIGS. 1 to 3 wherein the recess is containing an implant.
Figure 5:
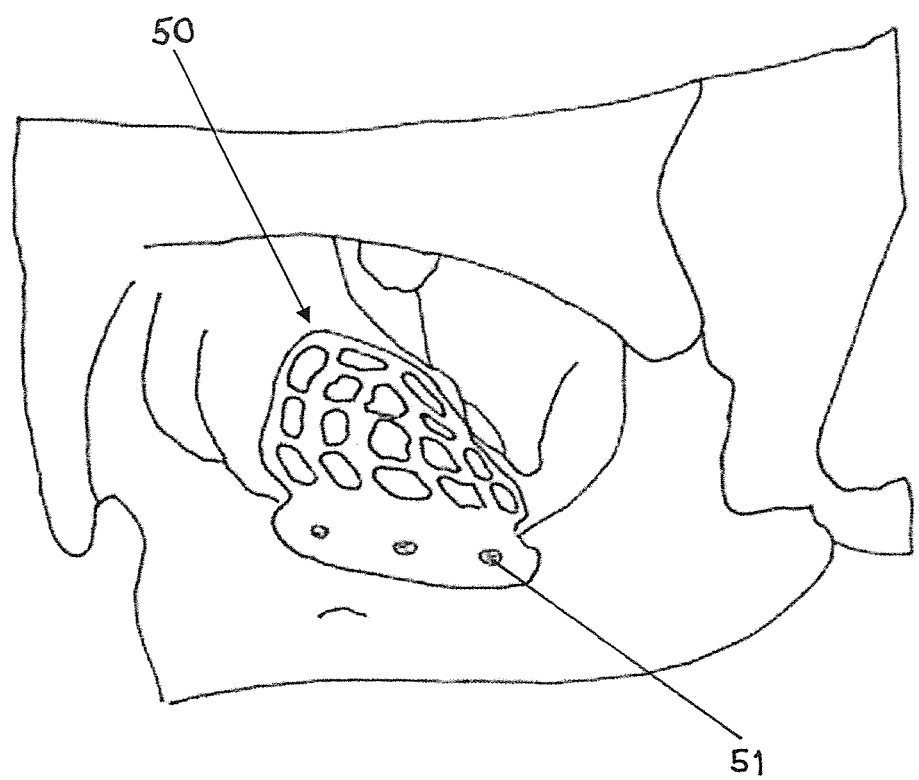
FIG. 5 illustrates the implant once implanted into the orbit to be treated.

FIGS. 4 and 5 illustrate an embodiment of the method for manufacturing a patient customized implant 50 using the auxiliary device 40 comprising the following alternative steps:

8) Biodegradable and biocompatible resin, or alternatively a standard implant material like a meshed titanium implant is positioned in the recess 42 of the auxiliary device 40 and shaped according to the form given by the recess 42 (FIG. 4).
   a) In case of using a biodegradable and biocompatible resin, it is preferably available in a semi solid, moldable state when starting the implant contouring process. The material is fitted into the recess 42 of the auxiliary device 40 and transferred to a solid state after having accomplished the implant contouring process. The change of the physical state could be achieved using a photocuring composition (e.g. methacrylated organic oligomers) or through soaking and leaching out of a biocompatible solvent (e.g. N-methyl-2-pyrrolidone) and precipitation of a polymeric composition insoluble in water. Before application the resin material is preferably available as a semi rigid matrix sheet. In case of using a photocuring composition the matrix sheet is preferably covered by non-light-transmissive lamination sheets to allow for its storage in a semi-rigid state. A prefabricated solid matrix portion with screw holes incorporated may be connected to the moldable part. The prefabricated portion allows for screw fixation near the orbital rim.
   b) In case of using a standard titanium mesh preferably a cutter is used to adapt the implant boundaries according to the borders of the recess 42 in the auxiliary device 40 defined by the inlay 35 of the computer template 30. Shape adaption is preferably achieved through press fitting the implant 50 to the bottom of the recess 42 of the auxiliary device 40. In a further embodiment of the invention a second auxiliary device 40' (rapid prototyping device) may be manufactured and temporarily fixed to the first auxiliary device 40 (rapid prototyping device). Hence a thicker, reinforced construct is available when the implant manufacturing/adjustment is in progress.

FIG. 5 illustrates an embodiment of the method for the treatment of orbital defects by using the patient customized implant 50. During intraoperative placement (FIG. 5) the implant 50 is temporarily fixed to the auxiliary device 40 (rapid prototyping device) with the auxiliary device 40

(rapid prototyping device) fitted to the borders of the defect and to the intact parts of the orbit inferior orbital rim.

According to Jaquiéry et al. accuracy of orbital reconstruction is one important factor to obtain best functional outcome, but other determinants like displacement and/or atrophy of intramuscular cone fat should be considered. This requires an additional volume i.e. a spacer or spacers to be positioned onto the customized implant 50.

Jaquiéry C., Aeppli C., Cornelius P., Palmowsky A., Kunz C., Hammer B. "Reconstruction of orbital wall defects: critical review of 72 patients", Int J Oral Maxillofac Surgery 2007, Mar. 36(3): 193-9, Epub 2007 Jan. 22.

In a further embodiment a holding extension 41, integrated in the auxiliary device 40 (rapid prototyping device) as an additional design feature facilitates manual placement of the implant 50. The holding device 41 is designed to allow a standard surgical instrument to be used, i.e. a clamp, to manually place the implant.

In another embodiment of the invention the implant 50 may be positioned onto the defect without the auxiliary device 40 (rapid prototyping device) or just with a part of it, e.g. just including the parts fitting to the inferior orbital rim and/or the holding extension 41. This would minimize the space required for intraoperative placement; thus be particularly helpful in conditions with limited access and visibility.

In a further embodiment of the invention the recess 42 of the auxiliary device 40 (rapid prototyping device) or the implant 50 itself may contain design features allowing for over contouring of the implant. This design feature may be helpful for compensating loss of soft tissue volume, e.g. useful in conditions with significant soft tissue atrophy. Therefore the recess 42 of the auxiliary device 40 (rapid prototyping device) may be designed in an over contoured fashion or with a pull linkage incorporated allowing the implant 50 to be over contoured at a given site.

Alternatively, additional implant material may be directly fixed to the implant 50 for over contouring.

Implant fixation is preferably achieved using screw fixation, preferably by fixing the implant 50 with screws 51 near the orbital rim.

Following implant placement and fixation the auxiliary device 40 (rapid prototyping device) is detached and removed.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A method for manufacturing an auxiliary device suitable for receiving material for the manufacture of a patient customized implant, the method comprising steps of:
   1) obtaining 3D image data of a defect site of a patient's anatomy;
   2) generating a computer model of the defect site based on the 3D image data obtained in step 1 and 3D generic reference data using a computer and image processing techniques;
   3) virtually reconstructing the defect site and designing a model of the patient customized implant using the computer;
   4) generating a computer template for manufacturing the auxiliary device, wherein the computer template
      (i) is larger than the virtually reconstructed defect site and thus covers the virtually reconstructed defect site and also includes an overlay portion that extends beyond a periphery of the virtually reconstructed defect site, and
      (ii) comprises a recess that spans the virtually reconstructed defect site and has a shape and size suitable for receiving the material for manufacturing the patient customized implant; and
   5) manufacturing the auxiliary device as defined by the computer template generated in step 4 using 3D printing.

2. The method according to claim 1, wherein the recess is provided on a surface of the computer template that faces towards the virtually reconstructed defect site.

3. The method according to claim 1, wherein the recess is larger than the virtually reconstructed defect site and encompasses a shape of the virtually reconstructed defect site.

4. The method according to claim 1, wherein the 3D generic reference data comprise a 3D anatomic atlas.

5. The method according to claim 1, wherein the 3D generic reference data is obtained by mirror imaging of a healthy contralateral side of the patient's anatomy.

6. The method according to claim 1, wherein the 3D generic reference data comprise a 3D mean shape model.

7. The method according to claim 1, wherein the auxiliary device corresponds to a physical model of the computer template.

8. The method according to claim 7, further comprising a step of:
   removing the auxiliary device from the patient's anatomy.

9. The method according to claim 1, wherein the 3D printing technology is a rapid prototyping technology.

10. An auxiliary device obtained by the method according to claim 1.

11. The auxiliary device according to claim 10, wherein the auxiliary device is for fitment to an unaffected region of the patient's anatomy.

12. The auxiliary device according to claim 11, wherein the auxiliary device is configured for fitment to boundaries of the defect site of the patient's anatomy and to a respective anatomical shape in an inferior orbital rim region.

13. The auxiliary device according to claim 10, wherein the auxiliary device is comprises a holding extension facilitating manual implantation of the patient customized implant.

14. The auxiliary device according to claim 13, wherein the holding extension is configured to allow a standard surgical instrument to be used to manually position the patient customized implant.

15. The auxiliary device according to claim 10, wherein the auxiliary device has a peripheral projection for fitment to an unaffected region.

16. The auxiliary device according to claim 10, wherein the auxiliary device has a recess suitable to shape and size the patient customized implant.

17. A method for manufacturing a patient customized implant using an auxiliary device obtained by a method according to claim 1, said method comprising steps of:
   a) introducing a curable biocompatible resin in a recess of the auxiliary device in a moldable state and photocuring the resin once fitted into the recess of the auxiliary device;
   OR
   b) press-fitting an implant material into the recess of the auxiliary device.

18. A method for reconstruction of a part of patient's anatomy by using a patient customized implant manufactured by a method according to claim 17, the method comprising the step of:
   positioning the patient customized implant onto the defect of the patient's anatomy without the auxiliary device;
   or
   positioning the patient customized implant with a least a part of the auxiliary device.

19. The method according to claim 18, wherein the patient customized implant is positioned in the recess of the auxiliary device during implantation.

20. The method according to claim 18, further comprising a step of fixing the patient customized implant with screws to the patient's anatomy.

21. The method according to claim 18, wherein the auxiliary device has a peripheral projection for fitment to an unaffected region, and wherein a part of the auxiliary device that is used for positioning the patient customized implant includes the peripheral projection.

22. The method according to claim 18, wherein the auxiliary device includes a holding extension, and wherein a part of the auxiliary device used for positioning the patient customized implant includes the holding extension.

* * * * *